United States Patent [19]

Kamimura et al.

[11] 4,180,061
[45] Dec. 25, 1979

[54] ELECTRONIC SPHYGMOMANOMETER

[75] Inventors: Shinobu Kamimura; Hideki Yamamoto, both of Nagaokakyo, Japan

[73] Assignee: Omron Tateisi Electronics Co., Kyoto, Japan

[21] Appl. No.: 855,716

[22] Filed: Nov. 29, 1977

[51] Int. Cl.² ............................................. A61B 5/02
[52] U.S. Cl. ................................................. 128/681
[58] Field of Search .................. 128/2.05 M, 2.05 S, 128/2.05 P, 2.05 G

[56] References Cited

U.S. PATENT DOCUMENTS

| 3,651,798 | 3/1972 | Egli et al. | 128/2.05 M |
| 3,742,937 | 7/1973 | Manuel et al. | 128/2.05 P |
| 3,814,083 | 6/1974 | Fletcher et al. | 128/2.05 S |

Primary Examiner—George J. Marlo
Attorney, Agent, or Firm—Stevens, Davis, Miller & Mosher

[57] ABSTRACT

An electronic sphygmomanometer of simplified construction. Systolic and diastolic blood pressure are both indicated by the flashing of a light emission diode on receiving the Korotkov sound signals. A filtering circuit for passing Korotkov sound signals and eliminating pulse sound signals and other noise is used which has a passband with a low cutoff frequency of approximately 40 Hz with a sharp slope and high cutoff frequency of approximately 90 Hz with a gradual slope.

2 Claims, 2 Drawing Figures

ELECTRONIC SPHYGMOMANOMETER

BACKGROUND OF THE INVENTION

This invention relates to an electronic sphygmomanometer for electrically discriminating Korotkov sounds.

The typical recently developed electronic sphygmomanometer has a microphone incorporated in an inflatable cuff which occludes blood flow. The blood pressure of an individual is measured when the cuff is wrapped around the arm of an individual to position the microphone over or adjacent an artery below the blood-occluding portion of a cuff. The microphone receives Korotkov sounds, as well as pulse sounds and other external noise, and converts this to electrical signals. The Korotkov sound signals are discriminated through a filtering circuit and applied to the systolic blood pressure indicator and diastolic blood pressure indicator respectively. However, prior art sphygmomanometers require complex electrical circuits and are expensive.

Thus, it is an object of the present invention to provide a compact sphygmomanometer suitable for family use.

Another object of the present invention is to provide a sphygmomanometer utilizing a simplified electrical circuit.

DESCRIPTION OF THE PREFERRED EMBODIMENTS

Figure 1:
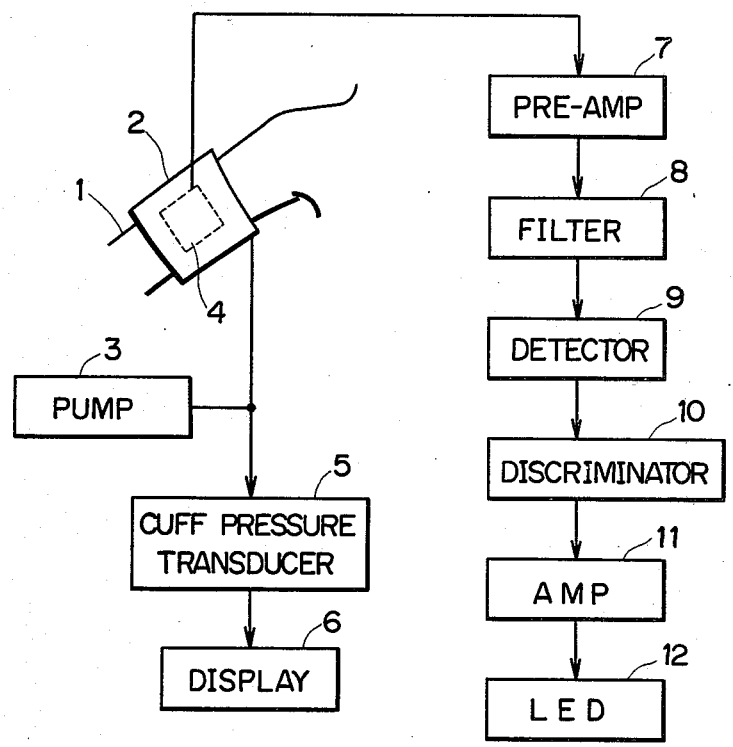
FIG. 1 shows a block diagram of one embodiment of the present invention.

Referring to FIG. 1, inflatable cuff 2 is wrapped around the arm of an individual. A microphone 4 is attached to the cuff 2. The cuff 2 is rapidly inflated by the pump 3 to a pressure above the point at which the blood flow is occluded, then the pressure in the cuff 2 is released at a substantially linear rate of approximately 3 mm Hg/sec. The pressure in the cuff 2 is converted to mechanical force by a transducer 5 and indicated by a display 6. The microphone 4 attached to the inside of the cuff 2 receives Korotkov sounds, as well as pulse sounds and other external noise, and converts these to electrical signals. Korotkov sound appears when the pressure in the cuff 2 is decreased to a certain extent which is called systolic blood pressure. With further decreasing the pressure in the cuff, Korotkov sound disappears at which pressure is called diastolic blood pressure.

The output signals of the microphone 4 are led to a preamplifying circuit 7 and are amplified.

Figure 2:
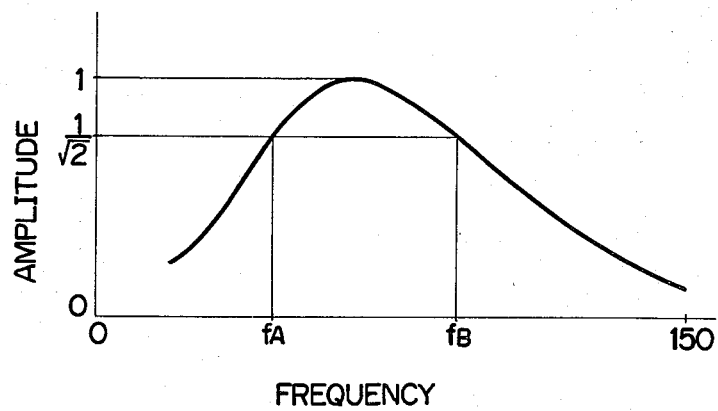
FIG. 2 shows the characteristics of a bandpass filtering circuit shown in FIG. 1.

The output of the pre-amplifying circuit 7 is fed to a bandpass filtering circuit 8 having a passband, as shown in FIG. 2, with a low cutoff frequency ($f_A$) of approximately 40 Hz with a sharp cutoff slope, for example 18 db/oct., and a 7 high cutoff frequency ($f_B$) of approximately 90 Hz with a gradual slope. The pulse sound frequency of an individual is generally below 20 Hz. On the other hand, the peak frequency of Korotkov sounds varies from approximately 40 Hz, at systolic pressure, to 90 Hz, at diastolic pressure.

Thus the pulse sound signals having an amplitude approximately 10 times larger than that of the Korotkov sound signals are eliminated through the filtering circuit 8 and other external noise out of the passband is also eliminated.

The output of the filtering circuit 8 is fed to the detecting circuit 9 and rectified. The output of the detecting circuit 9 is fed to a discriminating circuit, Schmidt trigger circuit, 10. The output of the discriminating circuit 10 is fed to an amplifying circuit 11 and amplified. A light emission diode, LED, 12 is energized by the output of the amplifying circuit 11. The LED 12 emits light on receiving the output of the circuit 11, in other words, on receiving Korotkov sound signals. The Korotkov sounds appears intermittantly, consequently the LED 12 emits light intermittantly during the first Korotkov sound (systolic pressure) to the last Korotkov sound (diastolic pressure).

The prior art sphygmomanometer requires a filter circuit having two passbands in which peak frequencies are approximately 20 Hz and 50 Hz, thus a complex circuit is required which is expensive. The present invention provides a sphygmomanometer utilizing a simplified circuit so that provides as phygmomanometer of low-cost, especially suitable for the family use.

What is claimed is:

1. An electronic sphygmomanometer comprising:
   an inflatable cuff;
   a pressure displaying means for displaying pressure in said cuff;
   a microphone attached to said cuff;
   an indicating means for indicating the appearance of Korotkov sounds; and,
   an indicating signal producing means for supplying indicating signals to said indicating means, including a preamplifying circuit for amplifying output signals of said microphone, a bandpass filtering circuit receiving the output of said pre-amplifying circuit and passing Korotkov sound signals, said bandpass filtering circuit having a passband with a low cutoff frequency of 40 Hz and a high cutoff frequency of 90 Hz, a detecting circuit for detecting said Korotkov sound signals, a discriminating circuit for discriminating output signals of said detecting circuit, and an amplifying circuit for amplifying the output of said discriminating circuit.

2. The electronic sphygmomanometer of claim 1, wherein said indicating means consists of a light emission diode which intermittently emits light in response to said detected Korotkov sound signals.

* * * * *